(12) United States Patent
Kozuch et al.

(10) Patent No.: US 9,105,072 B2
(45) Date of Patent: Aug. 11, 2015

(54) METHOD AND APPARATUS FOR AUTOMATED MULTI-USER MULTI-DURATION ACCESS TO EMERGENCY MEDICAL RECORDS

(75) Inventors: Michael J. Kozuch, Pleasanton, CA (US); Wallace J. Luke, III, Pleasanton, CA (US); Tom Eliaz, Menlo Park, CA (US)

(73) Assignee: Rule90 Technologies, Inc.

( * ) Notice: Subject to any disclaimer, the term of this patent is extended or adjusted under 35 U.S.C. 154(b) by 245 days.

(21) Appl. No.: 13/587,497

(22) Filed: Aug. 16, 2012

(65) Prior Publication Data

US 2014/0052471 A1    Feb. 20, 2014

(51) Int. Cl.
*G06Q 50/00* (2012.01)
*G06Q 50/24* (2012.01)

(52) U.S. Cl.
CPC .................................... *G06Q 50/24* (2013.01)

(58) Field of Classification Search
CPC ....... G06Q 50/22; G06Q 50/24; G06Q 10/10; G06F 19/322; G06F 19/328
USPC .......................................................... 705/2, 3
See application file for complete search history.

(56) References Cited

U.S. PATENT DOCUMENTS

| | | | |
|---|---|---|---|
| 2005/0165627 A1* | 7/2005 | Fotsch et al. | 705/3 |
| 2012/0191476 A1* | 7/2012 | Reid et al. | 705/3 |

* cited by examiner

*Primary Examiner* — Michelle L Le
(74) *Attorney, Agent, or Firm* — David S. Nagy (57) ABSTRACT

This invention is designed to offer ready access to an athlete's contact and health information for emergency responders at sporting events while providing improved security constraints to preserve the confidentiality of the athlete's information. The system offers new flexibility in the types of data fields that are collected, the duration of data availability, as well as to whom the data access privileges are granted.

16 Claims, 6 Drawing Sheets

| Name of event: | | |
|---|---|---|
| Date of event: | | |
| Activation date: | | |
| Expiration date: | | |

105
110
115
120

SERVICE PROVIDER SYSTEM

Setup For Event Organizer:
Contact & Medical Emergency
Options

Please check off information required for event:

- ▨ Name
- ☐ Address
- ▨ Telephone
- ☐ Date of Birth (D.O.B.)
- ▨ Insurance Carrier & No.
- ▨ Contact or Next of Kin
- ☐ Doctor (Primary)
- ▨ Allergies
- ▨ Medications
- ▨ Surgeries
- ▨ Illness

125

Download Bib Codes

Discrepancies between Emergency Access Sites

- First Name (Primary site): Michael  
  First Name (Secondary site): Mike } 505

- Telephone (Primary site): 555-555-5555  
  Telephone (Tertiary site): 555-555-5551 } 510

- Allergies (Primary site): none  
  Allergies (Secondary site): penicillin, peanuts } 515

- Allergies (Primary site): none  
  Allergies (Tertiary site): penicillin, peanuts } 520

Instructions
Click on the button to enable the secondary sites to match the primary site.

METHOD AND APPARATUS FOR AUTOMATED MULTI-USER MULTI-DURATION ACCESS TO EMERGENCY MEDICAL RECORDS

BACKGROUND OF THE INVENTION

1. Field of Invention

The present invention relates to the field of medical record keeping. The invention is more particularly related to accessing personal online health or medical records during an emergency for sporting events or during predefined time frames. Access to the emergency site is enabled by entering into a mobile device a URL or scanning a unique code that is printed on a sporting bib or other wearable artifact. The data types that are posted at the unique URL are specified by the event sponsors but are entered by the patient. Any number of emergency sites may be created for a single individual with variable times and periods of access duration.

2. Discussion of Background

In medical emergencies it is not uncommon for a victim to be incapacitated to the point of being unable to communicate with medical first responders. Of immediate concern to emergency medical responders is whether a patient or victim has any pre-existing conditions, allergies, or reactions to medical treatment that may be required. Even a simple aspirin may prove fatal to a victim with a pre-existing condition that adversely reacts with aspirin. Similarly, first responders might wish to know whether any pre-existing conditions may be the cause of or may have led to the medical emergency.

There have been suggestions that individuals carry a digital smart card, flash memory stick or some other implement that carries all their medical information. These devices could be carried on the person at all times, either in a wallet, pocket or purse. However, the drawback to this solution lies in losing these devices either through theft or misplacement. Should this occur, then all the personal health information or data for that person goes with it. The data may not necessary be lost, since there is most likely a backup at the source of the data, however with the loss of a device there is a loss of personal privacy. There are other situations where the devices require the user to enter a password or login code to view the information. While this is an important step in addressing security issues, should the patient be incapacitated, the device would not be helpful if first responders cannot acquire this information from an unconscious victim. Even flash drives or cards that contain a visible user ID and password fail to adequately protect the privacy of the device holder since anyone could access this information should the card be lost. A final drawback to carrying a card that resides in a purse, wallet or pocket that is hidden from view is that early responders might not legally be able to search for identifiable information on a person unless an officer of the law is present.

Many extreme sporting events, such as marathons, triathlons or long distance cycling events require participants to identify basic medical conditions during their registration process. Given the extreme nature of these events, participants are usually expected to be in proper physical shape to handle the duress of the events. They are also required to sign waivers that exempt event sponsors from any responsibility or liability in the event of injury or even death during the sporting activity. The unfortunate result of these waivers is that they inadvertently cause the event organizers to collect less medical information about their participants than might be necessary. Therefore, there is an important need for event organizers to collect more medical background of their participants in order to better treat them should they suffer a medical emergency, particularly if the victim is unconscious or unable to communicate.

Often, participants in extreme sporting events have a bib clipped on the front or back of their shirt or jersey that contains their participant number and perhaps their name, age, or even an emergency contact. Beyond the participant number, the available information on the participant is usually very limited.

In the event of an emergency first responders are tasked with stabilizing the injured athlete and often must call in the participant number on the bib to inquire about additional medical or contact information from the event organizer. Should the event organizers not collect sufficient health information as part of their registration process, then an important knowledge gap exists that may hinder or imperil treatment administered to the victim.

Therefore, a solution is required which allows event organizers to collect the information that they require for their medics as well their non-medical emergency responders, and which also permits critical information to be made available to early responders in an emergency during the event. Many responders now have Internet access through cellular phones or mobile devices, which access facilitates a solution to the problem of obtaining information that might not be carried on the subject of the emergency. Our solution capitalizes on the technologies available and satisfies the needs of event organizers in capturing the required information about the athlete participants while preserving the privacy and security of that information for the duration of the athletic event.

The following terms used in this application are defined as follows:

Athlete (or owner)—is a user who participates in an athletic event, who creates and generates the information in her personal health record. The athlete can also become a patient if injured or incapacitated in some way that requires the attention of emergency medical personnel or first responders. Referred to herein for convenience as "she," an Athlete can obviously be of either sex.

Event Organizers (or third party entity)—refers to the administrative organizers of a particular sporting or athletic event or service.

Sporting Event—generally refers to athletic events but does not exclude any kind of event that occurs over a limited time period. An example might be a long distance journey, trek, or any activity where the availability of a participant's medical information is not readily available.

Service Provider System—this refers to the web-based software service provider that runs the programs for gathering and synchronizing information. In this case we refer to the myLifeLog® system that feeds specific fields from a personal health record system (PHR) into an emergency access area.

Emergency Access Site—EAS (or subsidiary dataset)—refers to a private, secure electronic location that contains personal, social, demographic, medical, and/or contact information that is a subset of the information present in the master database as defined below. The information may be presented to first responders in the form of a website (in HTML, PDF or similar format), an audio recording, a direct data feed to the emergency system on the emergency responder vehicle, or even as a data feed directly to the hospital system once the emergency responder has authenticated communications with the hospital. The site is a location that is accessible through Internet, cellular, or voice platforms and is read-only. It cannot be altered from outside of the Service Provider System.

Personal Health Record—PHR (or master online database)—referring to electronic health records that are created by individuals. There are many systems in existence that collect demographic, medical history and contact information from individuals. In this case, we refer to the myLifeLog® personal health record system as described in co-pending U.S. patent application Ser. No. 13/211,308, the disclosure of which is hereby incorporated by reference.

SUMMARY OF THE INVENTION

We have invented a new technique and apparatus that enables event organizers to collect critical contact and medical information, and activate a private site containing this information about event participants. In the event of an emergency, first responders may quickly access critical medical information about a victim so that her treatment does not pose any harm to the victim. The present invention includes the design of an integrated system of components that provide a new approach and methodology to permit time-variable access to limited but critical medical or health information to ensure proper and immediate treatment, without the permanent loss of privacy of the individual.

The system gives individuals the ability to change or create new access to this personal information through an online (web-based) environment by way of a computer or mobile device. Multiple security access methods are possible including a single point and scan method, whereby a first responder uses a QR Reader on his smart phone to read an athlete-specific QR code or similar identifier on an athlete's racing bib or wristband in order to gain access to the emergency information; a point-scan-pin method, whereby a first responder uses a QR Reader on his smart phone to read an event-specific or athlete-specific identifier on a racing bib or wristband followed by the entry of the responder's license number, or similar responder identifier, and athlete's race number in order to gain access to the athlete's emergency information.

In one embodiment, the present invention provides a process that allows access to user-defined information until the user denies access by generating a new access code. Although the present invention focuses on accessing patient medical or health records, from a broader perspective, access to any system or facility can be made using similar processes so long as the supporting technology is available.

Portions of both the device and method may be conveniently implemented in programming on a general purpose computer, or networked computers, and the results may be displayed on an output device connected to any of the general purpose, networked computers, or transmitted to a remote device for output or display. In addition, any components of the present invention represented in a computer program, data sequences, and/or control signals may be embodied as an electronic signal broadcast (or transmitted) at any frequency in any medium including, but not limited to, wireless broadcasts, and transmissions over copper wire(s), fiber optic cable(s), and co-ax cable(s), etc.

BRIEF DESCRIPTION OF THE DRAWINGS

A more complete appreciation of the invention will be readily obtained by reference to the following detailed description when considered in connection with the accompanying drawings, wherein.

DESCRIPTION OF THE PREFERRED EMBODIMENTS

Figure 1:
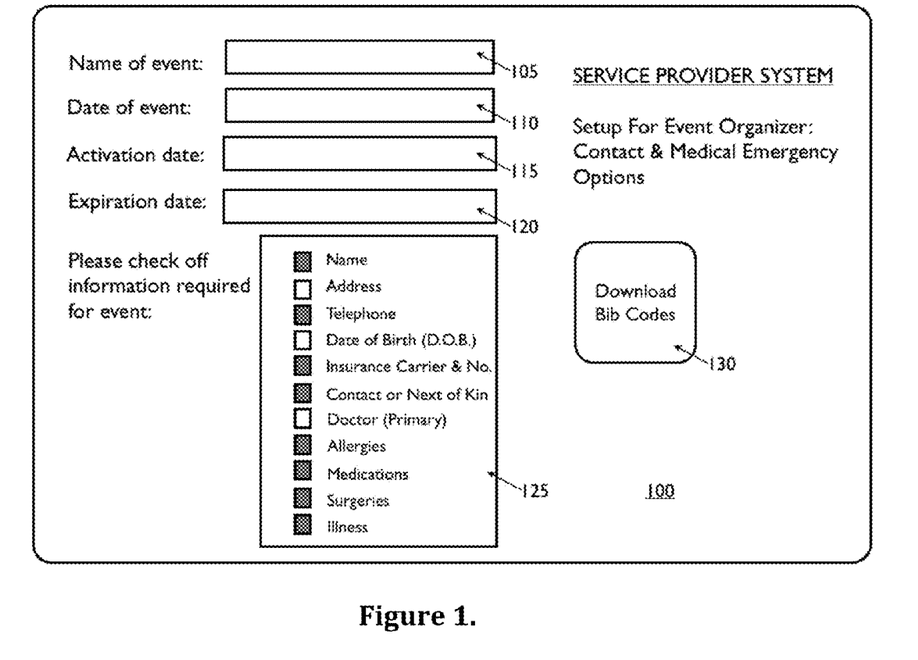
FIG. 1. myLifeLog® interface for event organizers. Event organizers select the athletic personal and medical information they want for their medical responders from a menu. We populate only what they need.

Referring now to the drawings, wherein like reference numerals designate identical or corresponding parts, and more particularly to FIG. 1 thereof, there is illustrated an overview of a web-based interface for Event Organizers (100). Once registered and logged in to the Service Provider System website, this interface is designed to allow the Event Organizers to enter the information that they will require from participating athletes in the event. Event Organizers would submit the name of the event (105), the date of the event (110), the activation date (115), and the expiration date (120). Both the activation date and expiration dates can be configured so that the difference between the two is no more than a pre-defined period in time (such as a week in total duration of active time centered around the date of the sporting event). Next, the Event Organizers are given the option to select any or all types of critical information listed (125) that are required to administer emergency aid. The list may include, but is not limited to, the name, address, address, telephone number, date of birth, age, insurance carrier(s), emergency contact(s) and their phone numbers, next of kin and their phone numbers, primary physician or specialist, allergies, current medications and treatments, recent surgeries, and current illnesses. Once the information on this interface is completed, the Service Provider System is ready to present an interface, either through a Sporting Event website or mobile device site, to athletes.

Figure 2:
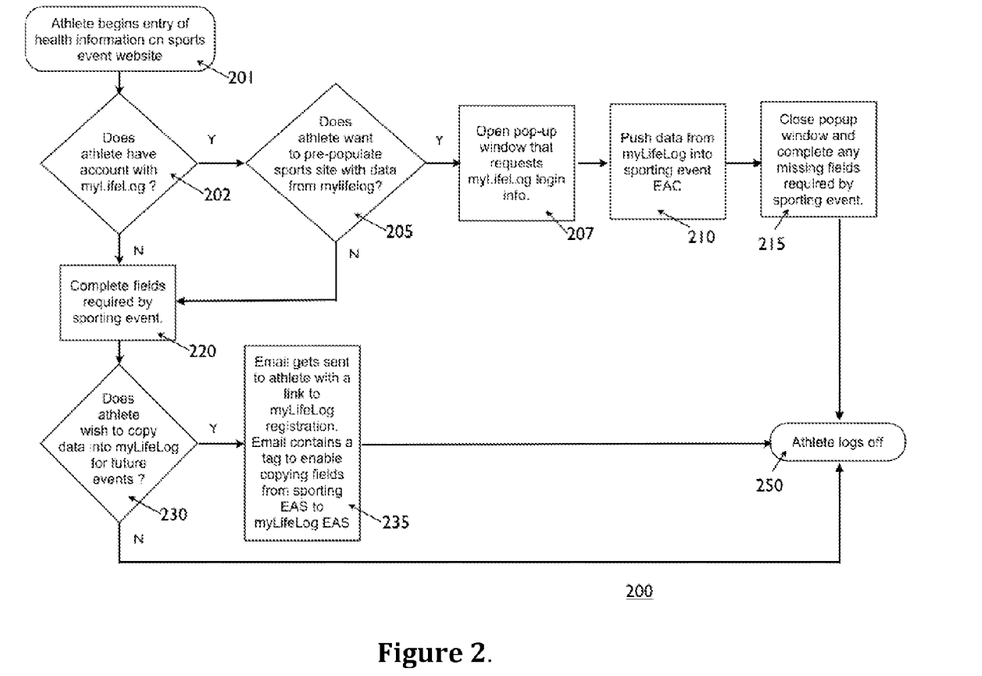
FIG. 2. Logic for the sporting Event Organizer interface for Athletes to register and enter their emergency medical and contact information.

In order to participate in Sporting Events, Athletes are usually required to register on the Event Organizer website. Many of these events now offer online registration via computer or a mobile device. As part of the online registration process, Athletes will often post their credit card information, contact details and minimal health information. The current system would replace legacy medical questionnaires and would instead follow a link to a secure site where emergency health information would be collected as depicted in FIG. 2. Another option is that the current site frames a window to another secure site. In the new window (201), the Athlete would follow a flow of questioning (200) that would address whether or not an Athlete already has an account with a particular Service Provider System (202) that supports or manages online personal health records, an example of which is myLifeLog®. The system would then ask if the Athlete would like to pre-populate or draw health information from the athlete's Personal Health Record (205). Should the Athlete wish to do so, then the system would request the Athlete's user information and password in order to enable the secure link (207) through a new window. Once the required login information is provided, an automatic feed is performed whereby the Service Provider System receives a request to forward the necessary information to the Sporting Event's Emergency Access Site (210) with a subset of the data that is contained in the Personal Health Record site. At this point, the registration popup window disappears and the prepopulated fields appear. The Athlete may then complete any fields that remain empty (215). Once the Athlete is satisfied with the data entries, then she may optionally choose to copy this added information to her Personal Health Record, and then may proceed to log off the system (250).

Should an Athlete who already has an account with a Service Provider System (205) choose not to pre-populate their event's Emergency Access Site, then all the required information will be directly asked for (220), whether or not it already exists in her Personal Health Record site. Once these responses are completed the Athlete will be prompted with a choice (230) to either push her data to her Personal Health Records or not. Should she choose to push this information to her health records, then a communication (e.g., an email, cellular text message, etc.) is automatically sent to her with a link to (235) her Personal Health Record site. Through this mechanism the Service Provider System obtains a tag that signals an instruction to copy data from the Event Organizer website to the PHR Emergency Access Site. Once all the data entry is completed, then the Athlete is prompted to log off the system (250).

Figure 3:
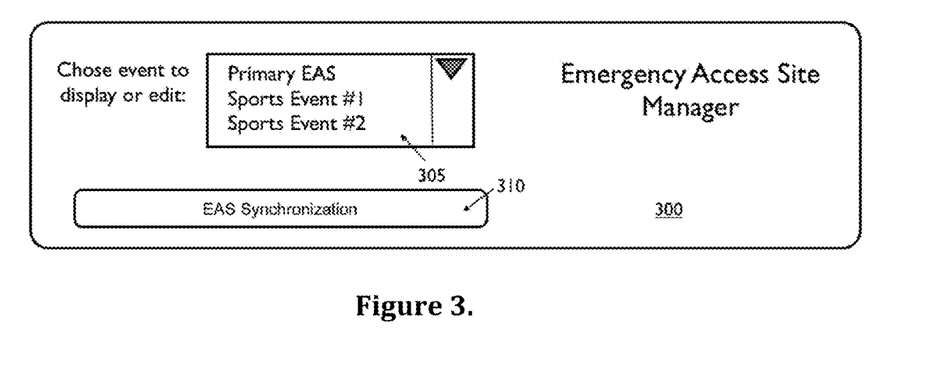
FIG. 3. Interface for athletes within the myLifeLog® personal health record system. Athletes select from a drop-down menu the Emergency Access sites they want to see in order to review the information that is accessible to first responders in particular events.
Figure 4:
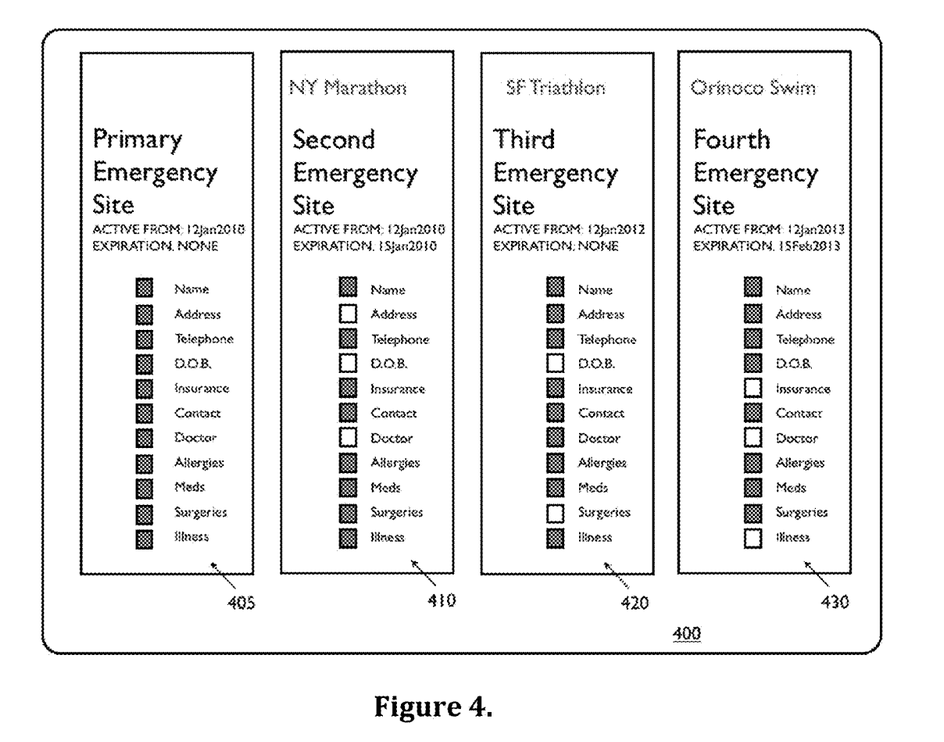
FIG. 4. Illustration of how multiple Emergency Access Sites for different sporting events can be active during different time frames and show only data fields that are required for a particular sporting event.

FIG. 3 shows how our system allows Athletes to view all the Emergency Access Sites that are registered (300). Within the Service Provider System, there is an interface, called EAS Manager, consisting of a drop-down menu (305) to allow Athletes to select one or all of the Emergency Access Sites to view. Once any one or all of the options are selected, then a display appears as shown in FIG. 4. This display illustrates what is shown in each EAS location (400). Individual EAS's will indicate which data-type is included in the actual EAS site (405, 410, 420, and 430).

Figure 5:
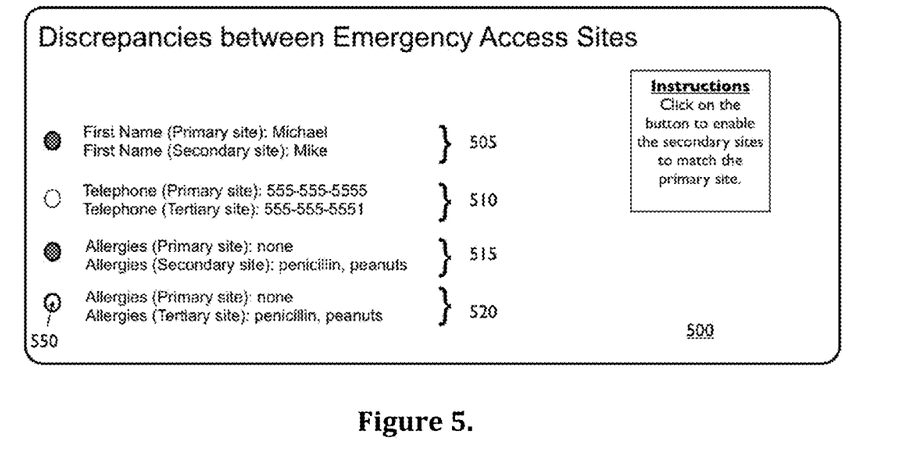
FIG. 5. Example of the myLifeLog® interface for Athletes that shows where discrepancies lie in their data between different Emergency Access Sites. Here they can synchronize or reconcile secondary sites to the primary Emergency Access Site. The only way to change information in the primary Emergency Access Site is to edit information in their personal health record.

Athletes are given the option to reconcile discrepancies between individual Emergency Access Sites (310) by clicking on the EAS Synchronize button in the EAS Manager (300). This function takes the Athlete to a new window as shown in FIG. 5. Discrepancies between individual fields in all the Emergency Access Sites are listed sequentially (500). As an example, an Athlete may have listed her complete first name in her personal health record (and primary EAS), yet she might have abbreviated or shortened it on a secondary EAS through the Event Organizer site (505). Clicking on the button will allow the secondary site to match the primary site. By not clicking on a button (550), it is possible that separate Emergency Access Sites can have different information listed for different categories. The only way a primary Emergency Access Site can be changed is through the PHR.

Once the registration period is closed, the Event Organizers are able to download a list of QR codes, bar codes, RFIDs, private URLs, or phone numbers with a private access code for each Athlete. This function is performed by the Event Organizer administrator through the Service Provider System's Event Organizer Setup Menu (100). The download consists of a name and a code for each Athlete as well as other participant identifiers. These codes can then be attached to or printed on Athletic bibs (FIG. 6), wristbands, or whatever Athlete identifier is used. The codes will not be active, i.e., will not permit access to the relevant EAS, until the time of the event, even though Athletes may receive the bibs several weeks prior to their Sporting Event.

Figure 6:
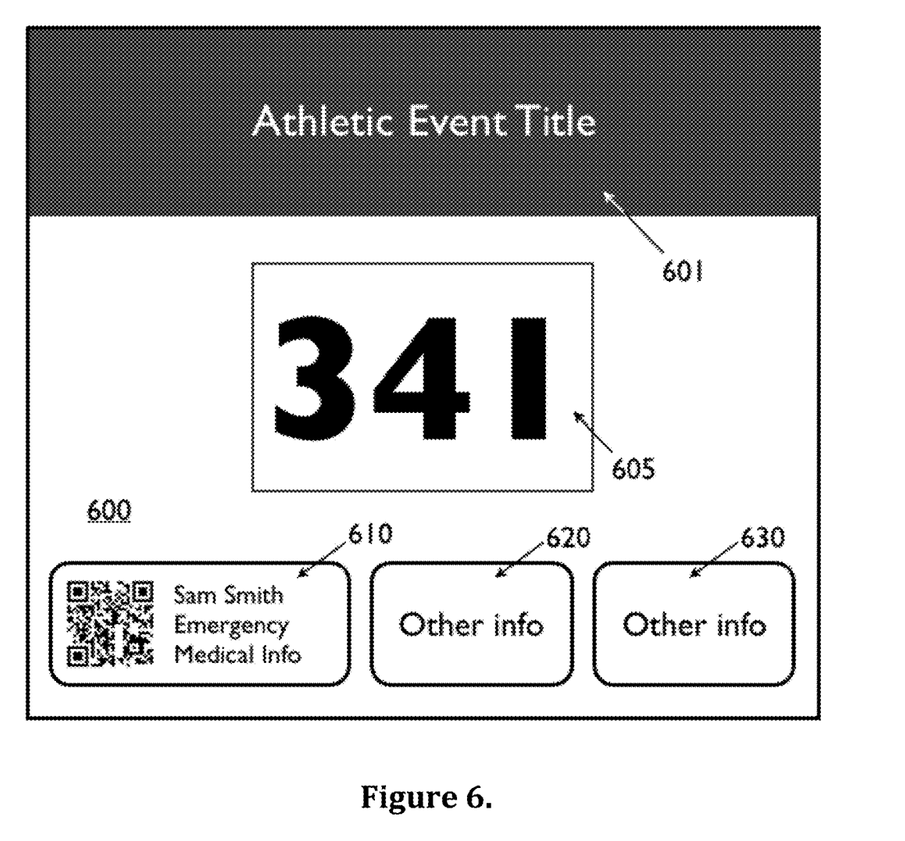
FIG. 6. Example of a sporting event bib that is worn by the Athlete.

Sporting bibs (600) typically consist of an identifier that is readily visible on the athlete so that bystanders or sporting officials can visually identify competitors from a distance. Bibs generally contain the title of the event (601), a unique participant number (605), and space for other information (620 and 630) such as sponsor logos. In some cases there is room for the Athlete's name and contact information, however this can easily be replaced with a unique code for emergency medical or health information (610).

In the event of an accident or injury, first responders may then scan the unique identifier on the bib with a portable scanning device such as a QR Reader on a smart phone or similar device, thereby immediately sending the image through in-channel communications such as MMS, SMS, etc., or using other protocols available such as email to an electronic address or number indicated on the emergency card. This would instantly relay the emergency contact and health information for the Athlete back to the smart phone. Quick and easy access to emergency information can be vital to saving a life.

The present invention may suitably comprise, consist of, or consist essentially of, any element of the various parts or features of the invention, and their equivalents as described herein. Further, the present invention illustratively disclosed herein may be practiced in the absence of any element, whether or not specifically disclosed herein. Obviously, numerous modifications and variations of the present invention are possible in light of the above teachings. It is therefore to be understood that within the scope of the appended claims, the invention may be practiced otherwise than as specifically described herein.

Plainly, this invention is applicable to the access of private medical records. While this invention was conceived to address pressing needs in the medical field, it can be seen that it is readily adaptable to other arenas in which entities require limited or full access to any such online record, application, document or image. Thus, while the descriptions herein have focused on medical applications, they can all be seen to have their analogs in other applications.

We claim:

1. A method for accessing records, comprising the steps of:
adapting a computer with specialized software programmed for creating a specialized web site;
utilizing such computer and its specialized software to create a primary web site programmed to receive, edit and allow access to database information, and further programmed to create one or more secondary web sites programmed to receive and allow access to database information transferred from the primary web site;
having an owner connect to the primary web site to create a master online database of the owner's records, containing information about the owner;
having one or more entities connect to the primary web site and identify specific information about the owner that each entity requires, and specify a time frame during which each entity requires such specific information;
having these specifications by the one or more entities cause the primary web site to create a secondary, read-only site comprising a subsidiary online dataset populated with such specific information about the owner for each entity, accessible by the entity only during the specified time frame; and having each entity access the secondary, read-only web site and the subsidiary online dataset with an internet-enabled device capable of displaying the records contained in the subsidiary dataset.

2. The method of claim 1, wherein the internet-enabled device is a tablet, smart-phone, or other mobile device.

3. The method of claim 1, wherein if not all of the specific information required by each entity is present in the master online database, upon creating the secondary web site and the subsidiary online dataset the owner is prompted to enter any missing information into the subsidiary online dataset, and is optionally further prompted to copy the missing information into the master online database.

4. The method of claim 1, wherein the internet-enabled device accesses said secondary, read-only web site and subsidiary online dataset by scanning a QR code or bar code or other optical tag, or by radio-frequency identification, or by accessing a private URL, or accessing a private telephone number.

5. The method of claim 4, wherein, in order for the internet-enabled device to be able to access said secondary, read-only web site and subsidiary online dataset, the operator of the internet-enabled device must supply an identifier which identifies said operator.

6. The method of claim 1, wherein the primary web site is further programmed to create a separate need-to-know site containing that fraction of the information in the master online database required by such an entity or entities, and populating any secondary, read-only web site and subsidiary online dataset from the information contained in the need-to-know site.

7. The method of claim 6, wherein the internet-enabled device is a tablet, smart-phone, or other mobile device, and wherein the internet-enabled device accesses said secondary, read-only web site and subsidiary online dataset by scanning a QR code or bar code or other optical tag, or by radio-frequency identification, or by accessing a private URL, or accessing a private telephone number.

8. The method of claim 6, wherein if not all of the specific information required by the entity is present in the master online database, upon creating the secondary web site and the subsidiary online dataset the owner is prompted to enter any missing information into the subsidiary online dataset, and is optionally further prompted to copy the missing information into the master online database.

9. A system for accessing records, comprising:
a computer with specialized software programmed to create a specialized web site;
a primary web site, created with that computer and its specialized software, programmed to receive, edit and allow access to database information, and further programmed to create one or more secondary web sites programmed to receive and allow access to database information transferred from the primary web site;
a master online database of an owner's records, containing information about the owner, created on or uploaded to the primary website;
a request from an entity to the primary web site, identifying specific information about the owner that the entity requires, and specifying a time frame during which the entity requires such specific information;
creation by the primary web site of a secondary, read-only web site comprising a subsidiary online dataset populated with such specific information about the owner, accessible only by the entity and only during the specified time frame; and
accessing by the entity of the secondary, read-only web site and the subsidiary online dataset with an internet-enabled device capable of displaying the records contained in the subsidiary dataset.

10. The system of claim 9, wherein the internet-enabled device is a tablet, smart-phone, or other mobile device.

11. The system of claim 9, wherein if not all of the specific information required by each entity is present in the master online database, upon creating the secondary web site and the subsidiary online dataset the software delivers a prompt for the entry of any missing information into the subsidiary online dataset, and optionally further prompts the copying of any missing information into the master online database.

12. The system of claim 9, wherein the internet-enabled device accesses said secondary, read-only web site and subsidiary online dataset by scanning a QR code or bar code or other optical tag, or by radio-frequency identification, or by accessing a private URL, or accessing a private telephone number.

13. The system of claim 12, wherein, in order for the internet-enabled device to be able to access said secondary, read-only web site and subsidiary online dataset, the operator of the internet-enabled device must supply an identifier which identifies said operator.

14. The system of claim 9, wherein the primary web site is further programmed to create a separate need-to-know site containing that fraction of the information in the master online database required by such an entity or entities, and populating any secondary, read-only web site and subsidiary online dataset from the information contained in the need-to-know site.

15. The system of claim 14, wherein the internet-enabled device is a tablet, smart-phone, or other mobile device, and wherein the internet-enabled device accesses said secondary, read-only web site and subsidiary online dataset by scanning a QR code or bar code or other optical tag, or by radio-frequency identification, or by accessing a private URL, or accessing a private telephone number.

16. The system of claim 14, wherein if not all of the specific information required by each entity is present in the master online database, upon creating the secondary web site and the subsidiary online dataset the software delivers a prompt for the entry of any missing information into the subsidiary online dataset, and optionally further prompts the copying of any missing information into the master online database.

* * * * *